(12) United States Patent
Obrebski (10) Patent No.: US 9,603,701 B2
(45) Date of Patent: Mar. 28, 2017

(54) FLEXIBLE ARTIFICIAL LENS ACCOMMODATED BY MEANS OF PRESSURE OR ELECTRICAL CONDICTIVITY

(75) Inventor: Andreas Obrebski, Duesseldorf (DE)

(73) Assignee: CARL ZEISS MEDITEC AG, Jena (DE)

( * ) Notice: Subject to any disclaimer, the term of this patent is extended or adjusted under 35 U.S.C. 154(b) by 988 days.

(21) Appl. No.: 10/590,430

(22) PCT Filed: Apr. 6, 2005

(86) PCT No.: PCT/EP2005/003618
§ 371 (c)(1),
(2), (4) Date: Jun. 18, 2007

(87) PCT Pub. No.: WO2005/096999
PCT Pub. Date: Oct. 20, 2005

(65) Prior Publication Data
US 2008/0039937 A1    Feb. 14, 2008

(30) Foreign Application Priority Data
Apr. 7, 2004   (DE) .................. 10 2004 017 283

(51) Int. Cl.
*A61F 2/16* (2006.01)
(52) U.S. Cl.
CPC .......... *A61F 2/1613* (2013.01); *A61F 2/1635* (2013.01); *A61F 2250/0018* (2013.01)
(58) Field of Classification Search
CPC ................................ A61F 2/16; A61F 2/1613
USPC .......................................................... 623/6.32
See application file for complete search history.

(56) References Cited

U.S. PATENT DOCUMENTS

| | | | |
|---|---|---|---|
| 4,477,158 A * | 10/1984 | Pollock | G02B 3/12 351/159.04 |
| 4,731,078 A | 3/1988 | Stoy et al. | |
| 4,816,031 A * | 3/1989 | Pfoff | 417/413.3 |
| 5,443,506 A * | 8/1995 | Garabet | 623/6.13 |
| 5,659,330 A | 8/1997 | Sheridon | |
| 6,117,171 A | 9/2000 | Skottun | |
| 6,369,954 B1 | 4/2002 | Berge et al. | |
| 6,730,123 B1 * | 5/2004 | Klopotek | 623/6.22 |
| 7,122,053 B2 * | 10/2006 | Esch | 623/6.13 |
| 7,147,865 B2 * | 12/2006 | Fishman et al. | 424/427 |
| 2005/0203613 A1* | 9/2005 | Arney et al. | 623/1.42 |

(Continued)

FOREIGN PATENT DOCUMENTS

EP     0 356 050 A1    2/1990
WO    WO 01/97742 A2    12/2001

(Continued)

*Primary Examiner* — Corrine McDermott
*Assistant Examiner* — Joshua Levine
(74) *Attorney, Agent, or Firm* — Kriegsman & Kriegsman (57) ABSTRACT

An artificial lens for an eye (10) is described. According to the present invention, an artificial lens for an eye is now provided, in which the focal width can change. This is realized according to the invention by providing the artificial lens with two or more media (12, 13) that are flexible in shape as lens elements and that the two media that are flexible in shape stand in direct contact with one another. The media that are flexible in shape are preferably disposed in an uptake container forming a lens body (11).

30 Claims, 4 Drawing Sheets

(56) References Cited

U.S. PATENT DOCUMENTS

2006/0244902 A1* 11/2006 Kuiper .................... G02B 3/14
　　　　　　　　　　　　　　　　　　　　　351/159.41

FOREIGN PATENT DOCUMENTS

| WO | WO 03/069380 A1 | 8/2003 |
| WO | WO 03/071335 A2 | 8/2003 |
| WO | WO 2004/054471 A2 | 7/2004 |

* cited by examiner

FLEXIBLE ARTIFICIAL LENS ACCOMMODATED BY MEANS OF PRESSURE OR ELECTRICAL CONDICTIVITY

BACKGROUND OF THE INVENTION

The present invention relates to an artificial lens for an eye, in particular, for a human eye.

In eye surgery, special applications already exist, in which the lens of an eye is replaced by an artificial lens. In the case of so-called cataract surgery, a lens of the eye—which is clouded, for example, due to the cataract—is replaced by an artificial lens. The lens of the eye is found inside a thin envelope, the so-called lens capsule. In order to remove the ocular lens, access to it is created by a thin cut made in the lens capsule and the ocular lens is next broken up into small pieces with a microsurgical instrument, and then these pieces are removed by means of an aspirating device. Then an artificial lens is inserted.

SUMMARY OF THE INVENTION

Artificial lenses that have been used up until now, however, always have had a fixed, unchangeable focal length. The object of the invention is thus to create an artificial lens for an eye, in which the focal length can be varied. This object is solved according to the invention by the artificial lens with the features according to the independent patent claim 1.

The artificial lens according to the present invention involves a lens implant, which can be inserted into the eye in place of the natural lens of the eye. It is provided according to the invention that the artificial lens has two or more media that are flexible in shape. In light of the present description, "flexible in shape" means that the media do not have a rigid surface, rather that the media can change their shape. It is also provided according to the invention that the two media that are flexible in shape stand in direct contact with one another.

The invention is not limited to a specific number of different media that are flexible in shape for the artificial lens, to specific materials for the media that are flexible in shape or to the specific states of the media that are flexible in shape. These may be selected in a targeted manner depending on the specific application and the desired optical properties for the artificial lens. Several nonexclusive examples are explained in more detail for this purpose in the further course of the description.

An adjustable lens will be created by the use of media that are flexible in shape, which form the lens elements of the artificial lens. In particular, it is now possible to create a lens that is variably adjustable in its focal length or focal width and which can be inserted into the eye as an artificial lens. This leads to a number of novel, advantageous fields of application, as will be explained in more detail in the further course of the description.

Advantageously, the at least two media that are flexible in shape are found in an uptake container, which then forms the lens body of the artificial lens. The uptake container can be shaped in the most varied manner. Several nonexclusive examples are explained in more detail for this purpose in the further course of the description.

Of particular advantage is the fact that the artificial lens is suitably formed now for accommodation due to the use of the media that are flexible in shape as the lens elements. "Accommodation" generally means the adjustment of the eye to a specific distance. In the case of an eye with normal vision, in a position of rest, the far point lies at infinity. Accommodation is the capacity of the eye to image close-lying objects on the retina, with an increase in refractive power. Accommodation is thus the change in the refractive power of a lens for "sharp viewing" of objects at fluctuating distances. This is also denoted the range of accommodation. The latter changes with increasing age. The reduction in the power of accommodation is the cause of presbyopia.

The reduction in the power of accommodation can now be equilibrated by the use of an artificial lens according to the present invention, since in this case it is possible to adjust its focal width.

Preferably, the artificial lens can have a defined, pre-adjusted refractive power. In this way, it is achieved that the artificial lens makes possible sharp vision in a range of specific distances, which is adapted to the defined, pre-adjusted refractive power. Each time depending on the person wearing such an artificial lens or depending on their preferences and requirements, the pre-adjusted refractive power may be different, so that the pre-adjusted distance ranges in which sharp vision is possible may be different, depending on the person.

In another configuration, the artificial lens can have a defined dynamic range of refractive power. The dynamic range indicates the number of diopters by which the refractive power of the artificial lens may vary. The invention is not limited to specific dynamic ranges. Advantageously, the dynamic range can comprise at least 1.5 diopters, preferably at least 2.5 diopters, and particularly preferred, at least 4 diopters.

If a focussing of the artificial lens by the defined pre-adjusted refractive power within the dynamic range is desired, this can be done by means of a suitable control device, which will be explained in more detail in the further course of the description. If sharp vision is desired outside the defined pre-adjusted refractive power or the defined dynamic range of the artificial lens, may also be effected—in particular, by adding a suitable aid for vision, for example, eyeglasses.

The artificial lens, in particular, has a pre-adjusted refractive power, which preferably has a value such that it makes sharp vision possible in a preferred distance range, or a range that is as large as possible—if the artificial lens has a given dynamic range.

First, an example of a preferred distance range will be described below. For example, a person working at a computer screen will prefer as much as possible a pre-adjusted value of the refractive power for a small dynamic range of the artificial lens (less than 2 to 3 diopters), which makes sharp vision possible for him in the range of several centimeters to a few meters. He may possibly prefer a pre-adjusted refractive power which permits sharp vision at the distance to the computer screen without activating a control device.

With larger dynamic ranges (for example, from 3 to 4 diopters), a refractive power for vision at greater distances (infinity) can be pre-adjusted, which corresponds to the natural state of a natural eye lens with a relaxed ciliary muscle and yet always permits reasonable vision in the near region.

Preferably the artificial lens can be pre-adjusted so that it makes possible sharp vision into infinity—without activating a control device.

Advantageously, the refractive power of the cornea will also be taken into consideration. Defects that may be present in it can be compensated by the artificial lens because the artificial lens makes available a constant additional refractive power. This constant additional refractive power need not be radially symmetric. Thus, for example, an astigmatism of the eye can be healed/compensated by a refractive power which is different in the X direction than in the Y direction.

The range of sharp vision can be selected differently, depending on the individual application, but should lie anywhere in the range between 1 cm and infinity. Of course, the refractive power may also be pre-adjusted in such a way that sharp vision will be possible at a distance that corresponds to a sub-region of the above-named distance range.

Advantageously, the media that are flexible in shape may contact one another, at least at their interfaces, and can be disposed so that they can be moved against one another. The artificial lens advantageously has an uptake container forming the lens body, in which two or more media that are flexible in shape are provided. The media that are flexible in shape are fixed in space and come into contact at least at an interface Fixing in space can be achieved by suitable fastening means. Several nonexclusive examples of suitable fastening means are explained in more detail in the further course of the description. Thus, for example, media that are flexible in shape can be used, which cannot be mixed.

In addition, means may be provided for changing the size and/or shape of the interface(s) between the media that are flexible in shape. Basically, the invention is not limited to specific media types. It is important only that the media are flexible in shape.

Advantageously, a control device may be provided for controlling the artificial lens. With such a control device, the artificial lens or the means for changing the size and/or shape of the interface(s) may be controlled in the desired way.

The artificial lens or the means for changing the size and/or shape of the interface(s) may be controlled in different ways. For example, it is conceivable that direct control can be effected by the eye muscles, e.g., the ciliary muscles. In this case, the eye muscle represents the control device and the artificial lens or the means for changing the size and/or shape of the interface(s) are connected or can be connected to the eye muscle.

It is also conceivable that the control device is formed for external manual or automatic control. For example, the control device may have an actuator and control can be affected by means of the actuator, in particular, an internal actuator. In this case, the invention is not limited to specific types of actuators. For example, these may involve microdrives, micropumps, micromotors and similar devices. In addition, a control is also possible via coupling with an autofocus system. In this case, the control device may have an autofocus system or may be formed as such an autofocus system. The autofocus system then transmits suitable regulating signals to the artificial lens. Autofocus systems are already known in and of themselves from the prior art, so that a detailed explanation can be omitted here.

As has already been mentioned above, the invention is not limited to specific configurations of the uptake container. For example, it may be provided that at least one boundary of the uptake container has a curved contour, at least in regions. In this way, the contour of the ocular lens to be replaced can be appropriately reproduced. One boundary of the uptake container, for example, involves a wall of the container.

Advantageously, one or more boundaries of the uptake container may be made transparent, at least in regions, in order to make it possible for light to pass through.

For example, at least one of the media that are flexible in shape can be made transparent, at least in regions. Advantageously, however, it is provided that all of the media that are flexible in shape are made partially transparent.

Advantageously, at least one medium that is flexible in shape can be applied at least at one bearing surface, at least in regions, within the uptake container. Here, the bearing surface can be found at different sites within the uptake container, so that the invention is not limited to specific variants of arrangement or formation. Several nonexclusive examples will be described below for this purpose. The bearing surface may involve, for example, at least one partial region of an outer wall of the container, perhaps the bottom of the container and/or a cover element and/or at least one lateral wall. In the case of the last-named variant, in particular, a configuration can be realized, in which the medium that is flexible in shape does not contact the bottom of the container, but is only applied at the lateral walls. Of course, configuration variants are also conceivable, in which the named bearing surface involves at least one partial region of an intermediate layer found in the inside space of the uptake container. The place where the medium that is flexible in shape is applied to the bearing surface of the uptake container is preferably formed of a transparent material, so that light impinging from the outside into the uptake container can radiate through the container walls and through the transparent media that are flexible in shape and found in the uptake container.

The invention is not limited to specific media types. For example, at least one medium that is flexible in shape may be a liquid. For example, it may be water, water containing saline additives and similar liquids. At least one medium that is flexible in shape can be comprised, for example, as an oil. Of course, the media that are flexible in shape may also be comprised in another way. It is important only that the media are flexible in shape. Thus, it is also conceivable, for example, that at least one medium that is flexible in shape is comprised as a type of gel.

Advantageously, it may be provided that at least one of the media that are flexible in shape is formed in the shape of one or more drops. A drop is generally understood to be a small quantity of medium of spherical or oval round shape, at least in regions.

Preferably, the media that are flexible in shape may have the same density or approximately the same density in order to exclude gravitational effects.

In another configuration, it may be provided that the media that are flexible in shape have the same density or approximately the same density in a specific temperature range. This temperature range is particularly adapted to the body temperature of the person who wears such an artificial lens. For example, the temperature range may lie between 30° C. and 45° C., preferably between 35° C. and 40° C., and particularly preferred between 36° C. and 38° C.

In addition, at least two of the media that are flexible in shape may have different optical properties throughout, for example, different optical indices. Thus it may be provided, for example, that they have different refraction numbers. It may thus be provided according to one advantageous—but not exclusive—example that one medium that is flexible in shape has a low refraction number (refractive index), while another medium that is flexible in shape has a high refraction number.

If the media that are flexible in shape are applied to a transparent bearing surface, for example, to an at least partially transparent boundary of the uptake container, these transparent regions of the bearing surface or of the container boundary preferably have the same refraction number or a similar refraction number to the applied medium that is flexible in shape. In this way, interrupted beam paths and undesired reflections are avoided. Of course, configurations may also be realized in which the respective refraction numbers are different. These designs may be utilized, for example, for setting particular optical effects.

Advantageously, it may be provided that a medium that is flexible in shape is moved over the means for changing the interface(s) in the direction of the respective other medium that is flexible in shape, such that the curvature of at least one interface between the two media that are flexible in shape is altered.

The invention is not limited to specific configurations for the means for changing the interface(s) between the media that are flexible in shape. Several nonexclusive examples will be indicated below for this purpose.

For example, the means for changing the interface(s) can be disposed annularly around a clear opening. In this case, the annular means may be formed as a single part or also in multiple parts, depending on the embodiment.

The clear opening may preferably correspond at least to the maximum pupil diameter of the eye for which the artificial lens is specified.

For example, it may be provided that the means for changing the size and/or shape of the interface(s) between the media that are flexible in shape are formed on the basis of electrowetting.

The principle of electrowetting by generating an electrical field can now make it possible for a first medium that is flexible in shape and a second medium that is flexible in shape to have different electrical conductivities. The medium with the smaller electrical conductivity, for example, an oil, can be disposed between the medium with the higher electrical conductivity, for example, water or water with additives, and at least one electrode. In this way, for example, it may be provided that the medium with the smaller electrical conductivity is disposed on one surface of a substrate, while the at least one electrode is disposed on the other surface of the substrate. Now, if an electrical field is applied between the at least one electrode and the medium with the higher electrical conductivity, the interface between the two media that are flexible in shape will be changed in this way.

Therefore, the means for changing the interface acts on an electrically conducting medium. By applying an electrical voltage, the wettability of a surface to which the electrically conducting medium is applied will be changed by this electrically conducting medium, so that the contour of the electrically insulating medium can also be changed indirectly in this way.

A transformation of this phenomenon is known, for example, from U.S. Pat. No. 5,659,330. A display device is described therein, in which individual drops of a conductor fluid are disposed on an insulating layer. Electrodes are present underneath this insulating layer. By means of the selective generation of an electrical field, the shape of any one drop of the conductor fluid can be varied, whereby a color pixel of an image is produced.

A solution as to how the principle of electrowetting can be generally utilized also in the field of lens elements is described in DE 698 04 119 T2. The invention depicted therein lies in the field of lenses with adjustable focus and therein, in particular, in the field of fluid lenses with an adjustable, electrically controlled focus. It will be possible with the lens element described therein to continually adjust the focus by means of so-called "electrowetting". According to this known solution, an optical element is provided for the variable adjustment of the focal length. Focal length generally involves the distance from the focal point to the plane of the optical element, for example, to the lens plane.

The known optical element is comprised of an uptake container, which contains a first, electrically conductive fluid as well as a drop of a second, insulating fluid. The two fluids are not miscible and are fixed in space in the uptake container. The two fluids contact each other at an interface. The drop of the second fluid is concentrically disposed around the optical axis of the optical element, wherein the optical axis also runs through a transparent region of the bottom of the uptake container. The first electrically conductive fluid is applied, at least in regions, to electrodes which are found inside the uptake container. In addition, at least one other electrode is provided, which is disposed outside of the container bottom. Here, this other electrode is disposed on the surface of the container bottom which is not facing the inside space of the container.

Finally, the known optical element has means for changing the interface between the fluids. An electrical field can be generated between the electrodes by this means. In this way, the wettability of the surface covered with the first, conductive fluid is altered, so the the shape of the drop of the second, insulating fluid is also altered by it. By varying the size and/or shape of the interface between the two fluids, the focus of the optical element can be continually adjusted. Similar solutions are known, for example, also from WO 03/071335 A2 as well as WO 031069380 A1.

In another configuration, the means for changing the interface(s) may be formed for acting on at least one of the media that are flexible in shape, wherein the means for changing the interface(s) are formed for producing a pressure on at least one of the media that are flexible in shape and wherein a medium that is flexible in shape is or can be displaced each time, and in particular, pressed, via this means, at least at an interface in at least one preferred direction, in the direction of another medium that is flexible in shape. Such means may be configured in a structurally simple, energy-saving manner, wherein such means often only require very small control voltages. The electrical conductivity of the media plays no role herein.

It is achieved by these means that a pressure will be exercised on the corresponding medium that is flexible in shape, so that it can be displaced, and in particular, pressed, at the interface in at least one preferred direction, in the direction of the respective other medium that is flexible in shape. This preferred direction preferably may be the optical axis of the artificial lens. The change in the focal width of the artificial lens and thus the change in the focal length is then produced roughly by pressing out one of the media that is flexible in shape in the direction of the other medium that is flexible in shape.

Thus, for example, it may be provided that the means for changing the interface(s) are formed for acting on a second medium that is flexible in shape and that the second medium that is flexible in shape is or can be displaced, and in particular, pressed, via this means, at least at an interface in at least one preferred direction, in the direction of a first medium that is flexible in shape. Additionally or alternatively it is also conceivable that the means for changing the interface(s) are formed for acting on a first medium that is flexible in shape and that the first medium that is flexible in shape is or can be displaced, and in particular, pressed, via this means, at least at an interface in at least one preferred direction, in the direction of a second medium that is flexible in shape.

In another configuration, it may also be provided that two media that are flexible in shape contact one another at two interfaces and that a medium that is flexible in shape is or can be displaced, and in particular, pressed, via the means for changing the interfaces, at one or both interfaces in at least one preferred direction, each time in the direction of another medium that is flexible in shape. In such a case, it is also possible, for example, that two preferred directions—one for each interface—an be selected. The preferred directions may be aligned opposite one another herein according to an advantageous enhancement.

In this way, it may be advantageously provided that a medium that is flexible in shape is displaced, and in particular, pressed, via the means for changing the interface(s), in the direction of another medium that is flexible in shape, such that the curvature of at least one interface is altered between the two media that are flexible in shape.

According to another configuration, at least one medium that is flexible in shape can be enclosed on all sides by another medium that is flexible in shape, wherein the means for changing the interface are formed for acting on at least one medium that is flexible in shape and wherein the means for changing the interface(s) are formed for producing a pressure on at least one of the media that are flexible in shape.

A special bearing surface is not necessary for this solution. Rather, a first medium that is flexible in shape and enclosed on all sides, and which advantageously has a spherical configuration in the initial state, is surrounded on all sides by another, second medium that is flexible in shape. The first medium that is flexible in shape may again involve, for example, water, and the second medium that is flexible in shape may advantageously involve a suitable oil. The two media that are flexible in shape advantageously have the same density, so that the second medium that is flexible in shape will be held in position inside the first medium that is flexible in shape and cannot sink, i.e., gravitational effects can thus be effectively excluded.

The means for changing the interface now exercises a pressure on at least one of the media that are flexible in shape. If the pressure is exercised on a first medium that is flexible in shape, the pressure will be transferred from the first to a second medium that is flexible in shape, so that the latter is compressed at the site where the pressure acts, which alters the size and/or shape of the interface between the two media that are flexible in shape. For example, the second medium that is flexible in shape can be changed from the initially spherical shape into an elliptical configuration. If the pressure is exercised on the second medium that is flexible in shape, the latter is extended against the first medium that is flexible in shape, so that the size and/or shape of the interface between the two media that are flexible in shape will also be altered in this case.

For example, the means for changing the interface(s) may be designed as a mechanical means, for example, in the form of a piston device, a stamping device, a cylinder device, or similar devices.

In another configuration, the means for changing the interface(s) may be designed, for example, also in the shape of at least one controllable membrane.

In the two above-named cases, for example, a direct control is offered for the eye muscles, e.g., the ciliary muscles. Insofar as the means for changing the interface(s) operate on a magnetic, electrical, or electromechanical basis, for example, a manual control can be effected from the outside, e.g., by moving a magnet, by controlling an electromagnet in a suitable way, or by similar means.

Here, of course, the invention is also not limited to specific drive types for the means for changing the interface. Therefore, it is possible that the means are designed to be electrically actuated. The voltages required in such a case lie in the range below one volt. Such means are thus particularly unobjectionable medically, save energy, and are cost-effective. Of course, other drive types for the means for changing the interface are also possible. It is conceivable, for example, that these means can be designed so that they can be actuated magnetically and/or electromagnetically and/or pneumatically and/or hydraulically and/or piezoelectrically, or by similar means.

In an advantageous embodiment, the actuation of the means for changing the interface can be controlled, for example, by means of the optical nerve of the eye. In such a case, the actuation of the means, in particular for a case of mechanical actuation, could also be effected by means of muscle parts around the eye.

The media that are flexible in shape can be fixed in space inside the uptake container by means of suitable fastening means. This is particularly important, since a beam path will pass through the artificial lens in a defined manner. The fixing in space is preferably provided by fastening means suitable for this purpose. However, the invention is not limited to specific types of fastening means.

Advantageously, the fastening means can be designed in the form of one or more different surface coating(s) inside the uptake container. Alternatively or additionally, the fastening means can be designed in the form of geometrical configurations, at least of regions of the uptake container. For example, these may involve projections, undercuts, recesses and similar forms.

The fastening means may be disposed and/or designed, for example, on at least one wall of the uptake container or on at least one region of at least one wall of the uptake container. It is likewise possible that the fastening means within the uptake container are disposed or designed, e.g., in the region of a bearing surface serving as an intermediate layer or the like.

Several advantageous, non-exclusive embodiment examples of suitable fastening means will be described below.

For example, the fastening means may be designed in the form of a particular surface configuration of the bearing surface and/or in the form of a particular surface state and/or in the form of a particular surface coating of the bearing surface and/or of the uptake container. For example, it may involve hydrophilic and/or hydrophobic coatings. The surface is thus advantageously configured in such a way that it can hold in position the applied medium that is flexible in shape. The particular surface state may be realized, for example, by means of a particular surface coating. Advantageously, a particular surface state may be provided relative to wettability. Of course, the invention is not limited to the named examples.

Thus, it may be provided, for example, that a part of the coating consists of a hydrophobic material and a part of the coating consists of a hydrophilic material, and that the two different materials are adjacent to one another along a boundary line. This boundary line, which is static, i.e., unchangeable, also forms a boundary line between the two media that are flexible in shape, one of which may advantageously be water or an aqueous solution, and the other of which may be oil, for example. It may be achieved by an appropriate coating of a surface that the position of the media that are flexible in shape does not change at the surface, so that the media are fixed in this region. A change of the interface between the two media is then possible in the way as described in more detail above, only in the region of the free interface between the two media, where the two media are in direct contact and which are found at a distance to the coated surface.

For example, it is conceivable that the fastening of the media that are flexible in shape is produced by a suitable selection of surface materials and/or local surface coatings within the uptake container, for example, the boundary or wall, respectively, of the uptake container. Likewise, the fixing in space of the media that are flexible in shape can be effected by applying a suitable, preferably predetermined voltage. In this case, it is advantageous if a first medium that is flexible in shape is formed as an electrically conductive medium and a second medium that is flexible in shape is formed as an electrically insulating medium. Of course, it is also conceivable to achieve the fixation in space by means of the structural configuration of the boundaries and/or intermediate layer(s) within the uptake container, for example, by providing these with suitable projections, edges, undercuts, recesses, and similar shapes.

The fastening means generally have the task of keeping unchanged the position of the media that are flexible in shape inside the uptake container, so that, in particular, a defined beam path can be produced by means of the artificial lens. The position in this case is understood to be relative to the wall of the uptake container and/or relative to a bearing surface within the uptake container.

Advantageously, it may be provided that an opening is made in the bearing surface of the uptake container—for example, in an intermediate layer—to which a medium that is flexible in shape is applied, and that the medium that is flexible in shape is fastened in the region of this opening. The opening, which advantageously corresponds to at least the maximum pupil diameter of the eye, is specific for the artificial lens and may particularly extend around an optical axis of the artificial lens, so that a light beam can pass through this opening and then through the media that are flexible in shape. In particular, all of the components of the artificial lens that are considered for this purpose are made transparent in the region of the opening.

In another configuration, means for stabilizing (stabilization means) the surface structure of at least one of the media that are flexible in shape may also be provided. These stabilization means can counteract an undesired breakdown of the contours of the media that are flexible in shape.

The stabilization means can hold together the surface structures of the media that are flexible in shape without essentially adversely affecting the optical quality of the artificial lens. In this way, stabilization is preferably effected by the use of external and/or internal structures. The stabilization means may be designed in the most varied manner, so that the invention is not limited to specific configurations. Several nonexclusive examples will be described below for this purpose.

Advantageously, the stabilization means may be provided, at least partially, in the region of the interface(s) between two—adjacent—media that are flexible in shape. It will also be included here, however, that a certain distance is present between the stabilization means and the interface(s), at least temporarily. This distance is selected such that the surface structure of the media that are flexible in shape cannot be disrupted.

For example, the stabilization means may be designed as at least one—in particular, elastic—foil, particularly as a perforated foil or similar material. In this case, the stabilization means involve a stabilization foil. If the stabilization means are designed as a permeable foil, it is not necessary that the media that are flexible in shape are immiscible. In another configuration, the stabilization means may have at least one element with a mesh structure, in particular with at least one—possibly elastic—structure made of threads and/or strips, or similar structures. Two or more of such elements may also be provided. Moreover, this also applies to the stabilization means formed as a foil. The elastic configuration of the at least one element is an optional feature, which is not absolutely necessary for executing the invention. In this case, the stabilization means involve, for example, a stabilization net. The stabilization net may advantageously be designed as a fine-mesh net made of threads or small strips, which hold together the surface structure of the medium that is flexible in shape and essentially do not adversely affect the optical quality. The individual threads are advantageously not too thick. Of course, a variation in thickness over the entire contour is also possible. In particular, in places where large loads act on the stabilization means, if the interface changes between the media that are flexible in shape, the threads can be thicker than, for example, in places where there is a smaller load.

The invention is not limited to specific materials which can be used to make the stabilization means. For example, suitable materials involve glass fibers, nylon and similar materials.

Advantageously, the stabilization means may be made transparent, at least in regions or partially. In this way, the optical quality of the artificial lens is not adversely affected by the additional stabilization means. Basically, however, non-transparent stabilization means are also conceivable, as long as these means do not adversely affect the function of the optical element, e.g., if these are not too thick.

The use of stabilization means by way of example for an artificial lens which has two media that are flexible in shape will be described below. Of course, the exemplary description can be transferred analogously also to artificial lenses that have more than two media that are flexible in shape.

The stabilization means may be disposed in the first and/or the second medium that is flexible in shape, depending on the configuration each time.

For example, the stabilization means may be disposed inside the second medium that is flexible in shape. In such a case, it is advantageously provided that the stabilization means are formed in a way so as to retain the second medium that is flexible in shape at the surface(s) of the stabilization means, particularly by means of a special surface coating of the stabilization means. For example, the stabilization means, e.g., a stabilization net, can be surface-coated with a material, or may consist of a material, which "retains" the second medium that is flexible in shape, e.g., in the form of an oil, at the surface, if the stabilization net is placed inside the second medium that is flexible in shape. The stabilization means are thus configured in such a way that their surface(s) are made/kept wettable for the second medium that is flexible in shape.

Likewise, it is possible that the stabilization means are disposed within the first medium that is flexible in shape. In such a case, the stabilization means can be formed, for example, in a way to repel the second medium that is flexible in shape from the surface(s) of the stabilization means, particularly by means of a special surface coating of the stabilization means. For example, the stabilization means, e.g., a stabilization net, can be surface-coated with a material, or may consist of a material, which repels the second medium that is flexible in shape, e.g., in the form of an oil, from the surface, if the stabilization net is placed outside the second medium that is flexible in shape. At the same time, the other medium that is flexible in shape, namely the first medium, in which the stabilization means are then found e.g., water, will not be repelled by the stabilization means.

Likewise, embodiments can be executed, in which stabilization means are disposed both within the first medium that is flexible in shape as well as also within the second medium that is flexible in shape.

Preferably, the stabilization means can have a prestress, at least in regions. This means that the stabilization means can be designed with a pre-formed contour. For example, it may be provided that this pre-formed contour is adapted to the contour of the interface between the two media that are flexible in shape, for example, in the region of the maximum and/or minimum extension of the second medium that is flexible in shape.

Advantageously, the stabilization means may have the same or at least a similar refractive index as the medium that is flexible in shape, in which they are found. If the stabilization means are found inside the second medium that is flexible in shape, their material should have the refractive index of the second medium that is flexible in shape, e.g., of an oil or similar substance. If the stabilization means are found outside the second* medium that is flexible in shape, they should preferably have the refractive index of the first medium that is flexible in shape, for example, water.

BRIEF DESCRIPTION OF THE DRAWINGS

The invention will now be explained in more detail based on the embodiment examples with reference to the attached drawings. Herein is shown.

DETAILED DESCRIPTION OF THE INVENTION

Figure 1:
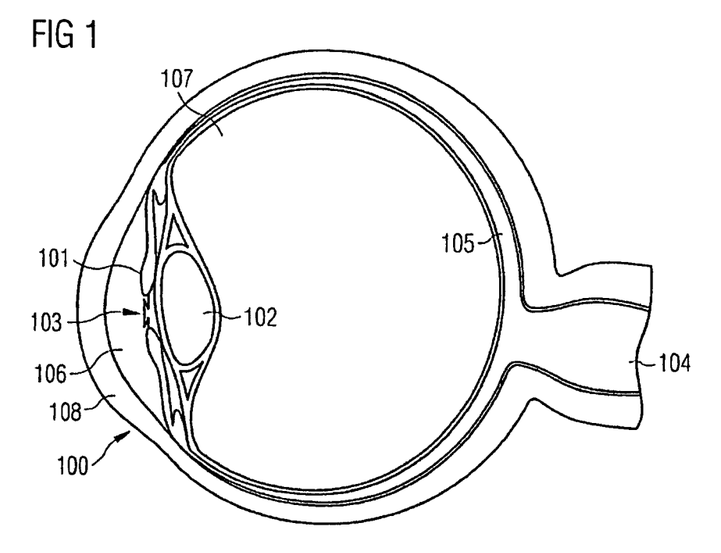
FIG. 1 a schematic representation of a human eye.

First of all, a human eye 100 is shown in general form in FIG. 1. Behind the cornea 108 is found the iris 101 with the pupil 103. The pupil 103 lies in front of lens 102. The chamber of the eye is found between cornea 108 and iris 101. In the back part of the vitreous body 107 lies the retina 105. Extending from there are also the central conduits 104.

The width of accommodation of the eye decreases with increasing age in humans. The reduction in the power of accommodation is the cause of presbyopia. "Accommodation" generally means the adjustment of the eye to a specific distance. In the case of an eye with normal vision, in a position of rest, the far point lies at infinity. Accommodation is the capacity of the eye to image close-lying objects on the retina, with an increase in refractive power.

By means of exchanging the lens 102 for an artificial lens (lens implant) according to the present invention, as it will be described below on the basis of several embodiment examples in combination with FIGS. 2 to 5, the reduction in the power of accommodation can now be equilibrated, since the focal width can be adjusted in the artificial lens.

Figure 2:
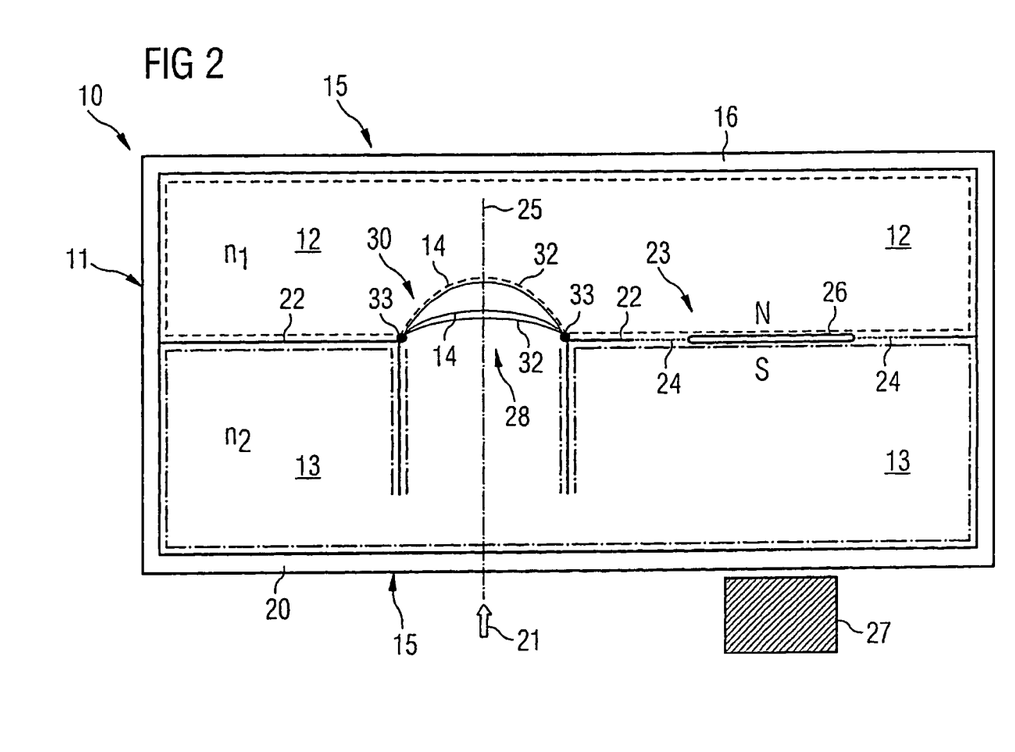
FIG. 2 a first example of embodiment of an artificial lens according to the present invention.

A first example of embodiment of an artificial lens 10 according to the present invention is shown in FIG. 2, which involves a lens with variable focal width. The representation shown in FIG. 2 involves an illustration of the fundamental principle of the function of artificial lens 10 with variable focal width. It is understood that such an artificial lens 10 can be adapted for use as lens 102 in an eye 100 (FIG. 1) by configuring the contours of the eye.

The artificial lens 10 shown in FIG. 2 is comprised first of all of an uptake container 11, which, among other things, is delimited by a bottom 20 of the container and a container cover 16 lying opposite to this. The bottom 20 of the container and the container cover 16 are boundaries 15 of the uptake container 11. The uptake container 11 represents the lens body of the artificial lens 10.

The optical axis 25, along which the beam path 21 of a light beam passes through the artificial lens 10, runs perpendicular to the bottom 20 of the container.

At least in a region around the optical axis 25, the bottom 20 of the container and also the container cover 16 each have a transparent region. Of course, it is conceivable that the entire container bottom 20 and the entire container cover 16 are made of a transparent material.

Within uptake container 11 are found two different media 12, 13 that are flexible in shape, which are lens elements of the artificial lens 10. The two media 12, 13 cannot be mixed with one another, they have different optical properties (different refractive numbers n1 and n2) and have at least a similar density. In addition, both media 12, 13 are transparent. In the present example of embodiment the media 12, 13 that are flexible in shape can involve liquids, wherein, for example, the first medium 12 can be designed as water and the second medium 13 as oil.

An intermediate layer, which again has an opening 28, is found inside uptake container 11. Like the transparent region of the container bottom 20, opening 28 is also made concentric around the optical axis 25 inside the intermediate layer 22. The opening 28 may correspond, for example, to the maximum pupil diameter of the eye for which the artificial lens 10 is specified.

In the example shown in FIG. 2, such surfaces within the uptake container 11, which are wetted with the first medium 12, are characterized by a dashed line, while those surfaces which are wetted with the second medium 13 are characterized by a dot-dash line.

The two liquids 12, 13 are fixed in space in uptake container 11 by suitable means, wherein the second liquid 13 is applied to the intermediate layer 22, which is formed as a bearing surface, at least in regions, within the uptake container 11. Thus the second liquid 13 is also fixed in the region of opening 28, so that the liquid 13, which has a drop form at least in the region of interface 14 between the first and second liquids 12, 13, extends concentrically around the optical axis 25.

A light beam 21 which impinges into artificial lens 10 thus first passes through the transparent region of the bottom 20 of the container, then the second liquid 13 as well as opening 28 in bearing surface 22 inside uptake container 11, then through the first liquid 12 and then a transparent region of the container cover 16. If the light beam 21 enters via the container cover 16, the beam path runs precisely in the reverse manner.

A change in the focal width of the artificial lens 10 now takes place in such a way that the size and/or shape of interface 14 is altered, for example, its curvature—between the two liquids 12, 13. This is provided by appropriately configured means 23. In the present example of embodiment, the means 23 for changing the interface 14 are designed in the form of a membrane 24, which forms a part of intermediate layer 22. On or in membrane 24 there is found at least one small magnetic or metal plate 26. This small plate 26 can be acted on by means of an electromagnet 27.

If the small plate 26 is formed as a small magnetic plate, it can be pulled in the direction of the bottom 20 of the container or in the direction of the container cover 16, depending on the polarity, when electromagnet 27 is actuated. If small plate 26 is formed as a small metal plate, it can be pulled when electromagnet 27 is actuated.

It is now possible to act directly on the liquid 13 by the means 23 for changing the interface 14. This is done in a way that the second fluid 13 is pressed at interface 14 against the first liquid 12 in at least a preferential direction—in the present example, in the direction of optical axis 25—in the direction of the first liquid 12. This is done in a particularly simple and energy-saving way by actuating the membrane 24.

In the initial state, the membrane 24 is found in its initial horizontal position. The second liquid 13 has a drop form on the bearing surface 22, wherein the interface 14 has a flat curvature between the liquids 12 and 13. This is shown by a solid line.

Now, if electromagnet 27 is actuated and the small plate 26 is pulled, for example, in the direction of the container bottom 20, this also leads to the fact that the membrane 24 is deflected in the direction of the container bottom 20. In this way, the second liquid 13 is pressed through opening 28, whereby the curvature of the interface 14 changes into an essentially more arched form, which is shown by a dashed line. The second liquid 13 is thus pressed in the direction of the optical axis 25 in the direction of the first liquid 12.

The means 23 for changing the interface can be controlled directly, for example, by means of the ciliary muscles of the eye, or also manually or automatically from outside. The control can also be carried out in a way that has already been explained in more detail above in the general part of the description.

In order to prevent a disturbance of the drop of the second liquid 13, e.g., by vibrations or similar phenomena, stabilization means 30 are provided. The stabilization means 30 may be a stabilization foil 32—for example, an elastic foil, in particular a perforated foil, around a stabilization net with a mesh-like or similar structure. The stabilization foil 32 is disposed on bearing surface 22 by means of suitable fastening elements 33.

Figure 3:
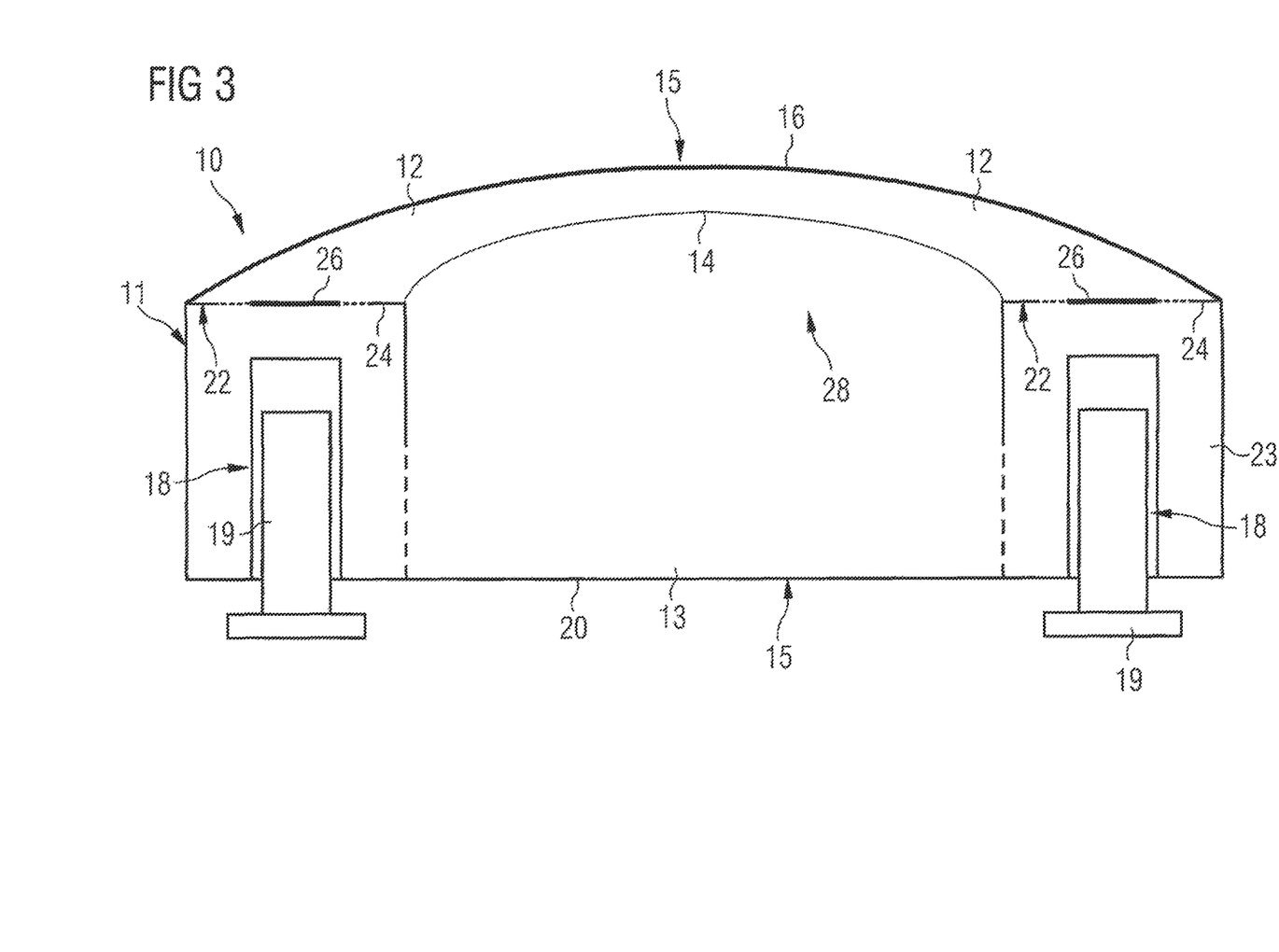
FIG. 3 a second example of embodiment of an artificial lens according to the present invention.
Figure 4:
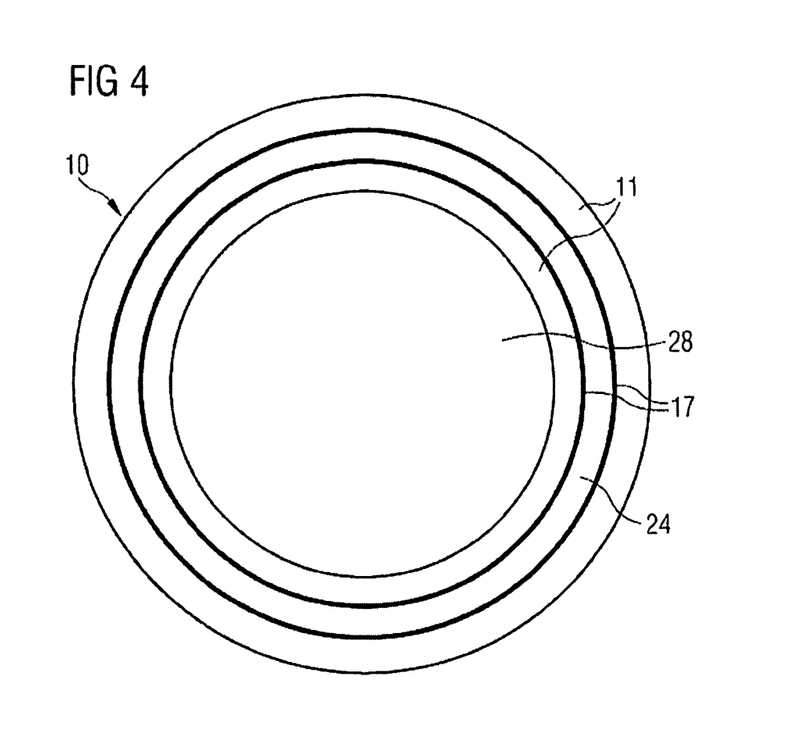
FIG. 4 a schematic top view onto the artificial lens shown in FIG. 3.
Figure 5:
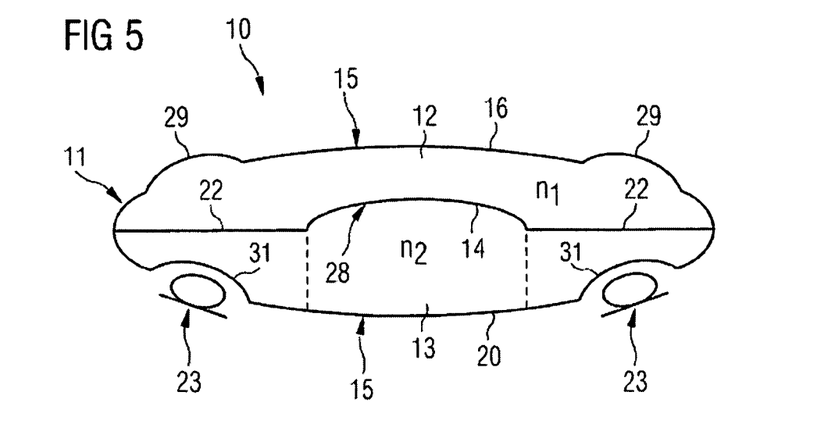
FIG. 5 a third example of embodiment of an artificial lens according to the present invention.

Two other embodiment examples of an artificial lens 10 according to the present invention are shown in FIGS. 3 to 5. The basic structure of the artificial lens 10 with uptake container 11 and the flexible media 12, 13 substantially corresponds to the embodiment shown in FIG. 2, so that in this respect reference is first made to the above discussion relative to FIG. 2. The same components here have been provided with identical reference numbers. In the embodiment examples according to FIGS. 3 to 5, means 23 for changing the interface(s) 14 are also provided between the media that are flexible in shape 12, 13, and these means are designed so as to be mechanically actuatable. Of course, configurations of the artificial lens 10 can also be provided, which function according to the principle of electrowetting, which has been described in more detail above.

The artificial lens 10 which are shown in FIGS. 3 and 4 have an uptake container 11 with a container bottom 20 and a container cover 16, which involve boundaries 15 of the uptake container 11, which in turn forms the lens body of the artificial lens 10. The container cover 16 in this case has a curved contour and is adapted in this respect to the contour of the ocular lens.

The first medium 12 that is flexible in shape, for example water, and the second medium 13 that is flexible in shape, for example oil, make common contact at an interface 14. Again, a bearing surface 22 is provided in the form of an intermediate layer. The intermediate layer 22 provides an opening 28. The two liquids 12, 13 are fixed in space in uptake container 11 by suitable means, wherein the second liquid 13 is applied to the intermediate layer 22, which is formed as a bearing surface, at least in regions, within the uptake container 11. Thus the second liquid 13 is also fixed in the region of opening 28, so that the liquid 13, which has a drop form at least in the region of interface 14 between the first and second liquids 12, 13, extends concentrically around the optical axis. In this respect, reference is also made additionally to the discussion in connection with FIG. 2. The opening 28 may have a diameter, for example, which at least corresponds to the pupil diameter of the eye which is to be implanted with the artificial lens. The opening 28 thus bounds the clear opening of lens 10.

As in the example of FIG. 2, the means 23 for changing the interface provide a membrane 24, but this time, however, it is disposed circularly around the opening (FIG. 4). The membrane may be a component of the intermediate layer 22 and can be connected to the uptake container 11. This may be carried out with suitable fastening means 17. Of course, the membrane 24 and the uptake container 11 may be combined into a single component. Each time depending on the type of actuation of membrane 24, the latter may again be provided with at least one small plate 26.

In the example according to FIGS. 3 and 4, the means 23 for changing the interface have a stamping device 18 with a moving stamp or plunger 19. This is also annularly disposed around the opening 28. For example, the stamp 19 may be magnetic, so that small plate 26 and thus membrane 24 is moved by its motion. The displacement of membrane 14 acts on the liquids 12, 13 in the way described in FIG. 2, so that the contour of its interface 14 changes. In this way, the focal width of the artificial lens 10 is also changed. Of course, it is also conceivable that the means 23 provide a piston device, whereby the movement of the piston already leads to a displacement of liquid 13. In another configuration, the movement of the membrane could also be produced via a piezoelement or similar component.

The means 23 for changing the interface again can be controlled directly, for example, by means of the ciliary muscles of the eye, or also manually or automatically from outside. The control can also be carried out in a way that has already been explained in more detail above in the general part of the description.

Finally, in FIG. 5, an artificial lens 10 is shown, which corresponds in the form of its outer appearance to lens 102 of an eye 100 (FIG. 1). In its basic structure as well as its basic function, lens 10 corresponds to those lenses which are shown in FIGS. 2 to 4. The same components are thus provided with identical reference numbers. In addition, reference is made to the corresponding details relative to these figures.

Artificial lens 10 provides an uptake container 11 forming the lens body 11, in which two media 12, 13 that are flexible in shape are found, which are basically separated from one another by a dividing wall 22. The media 12, 13 that are flexible in shape again involve liquids, in the case of medium 12, water, and in the case of medium 13, oil. The media 12, 13 that are flexible in shape have different refractive numbers n1 and n2. The dividing wall 22 or the intermediate wall has an opening 28, through which medium 13 can enter into the region of medium 12. The two media 12, 13 contact one another at an interface 14.

Both the container bottom 20 as well as the container cover 16, which involve boundaries 15 of the uptake container 11, are formed of a transparent material. The container cover 16 has at least one flexible region 29. The container bottom 20 has at least one flexible region 31. The flexible regions 29 serve for providing pressure compensation.

Means 23 for changing the interface are disposed in the flexible regions 31 of the container bottom. For example, these means may involve an annular arrangement as shown in FIGS. 3 and 4, wherein the invention is not limited, of course, to this concrete configuration.

By actuating means 23 for changing the interface, the flexible regions 31 of the container bottom 20 are pressed inwardly into the uptake container. This brings about a displacement of medium 13, which can only escape through opening 28. This leads to a change in the contour of interface 14 between media 12 and 13 and thus to a change in the focal width of the artificial lens 10. A corresponding equilibration of the pressure can be brought about in the region of medium 12 via the flexible regions 29 in the container cover 16.

Here also, the means 23 for changing the interface can be controlled directly, for example, by means of the ciliary muscles of the eye, or also manually or automatically from outside. The control can also be carried out in a way that has already been explained in more detail above in the general part of the description.

A novel artificial lens for an eye can be created by the present invention. Previously, artificial lenses implanted into an eye within the framework of eye surgery have always had a fixed, unchangeable focal width. According to the present invention, an artificial lens for an eye is now provided, in which the focal width can change. This is realized according to the invention by providing the artificial lens with two or more media that are flexible in shape as lens elements. The media that are flexible in shape are preferably disposed in an uptake container forming a lens body. In this way, new fields of application for artificial lenses are created, for example, the elimination of presbyopia. Of course, the artificial lenses according to the invention may also find use in applications that already exist today—e.g., in cataract surgery.

LIST OF REFERENCE NUMBERS

10 Artificial lens
11 Uptake container
12 First medium that is flexible in shape
13 Second medium that is flexible in shape
14 Interface between the media
15 Boundary of the uptake container
16 Container cover
17 Fastening means
18 Stamping device
19 Stamp or plunger
20 Container bottom
21 Direction of light beam
22 Bearing surface (intermediate layer)
23 Means for changing the interface
24 Membrane
25 Optical axis
26 Small plate
27 Electromagnet
28 Opening
29 Flexible region of the container cover
30 Stabilization means
31 Flexible region of the container bottom
32 Stabilization foil
33 Fastening element
100 Eye
101 Iris
102 Lens
103 Pupil
104 Central conduits
104 Retina
106 Chamber of the eye
107 Space for the vitreous body
108 Cornea

The invention claimed is:

1. An artificial lens for an eye, said artificial lens being a lens implant that is inserted into an eye in place of the natural lens of the eye, said artificial lens being characterized in that it has a lens comprising of two or more media that are flexible in shape that come into direct contact with one another, in that the at least two media are disposed in a lens body, in that the media that are flexible in shape contact on at least one interface and are disposed so that they can be displaced relative to one another, in that the media that are flexible in shape are each formed as a liquid, in that it has means for changing at least one of the size and shape of the at least one interface between the media, in that the media are applied to at least one bearing surface, at least in regions, said bearing surface being an intermediate layer inside said lens body, said intermediate layer having an opening which is made concentric around an optical axis of said artificial lens, said opening corresponding to the maximum pupil diameter of the eye for which the artificial lens is specified, and in that one of the media that are flexible in shape is made in the form of a drop, said medium being fixed in the region of said opening.

2. The artificial lens according to claim 1, further characterized in that the at least two media that are flexible in shape are disposed in an uptake container forming the lens body.

3. The artificial lens according to claim 2, further characterized in that at least one boundary of the uptake container has at least one arched contour, at least in regions.

4. The artificial lens according to claim 2, further characterized in that at least one boundary of the uptake container is made transparent, at least in regions.

5. The artificial lens according to claim 2, further characterized in that one or more boundaries of the uptake container are made of a flexible material, at least in regions.

6. The artificial lens according to claim 2, further characterized in that the fixation in space of the media that are flexible in shape inside the uptake container is provided by fastening means.

7. The artificial lens according to claim 6, further characterized in that the fastening means are designed in the form of at least one of one or more different surface coating(s) inside the uptake container and a geometric configuration at least of regions of the uptake container.

8. The artificial lens according to claim 1, further characterized in that the latter is formed in a suitable manner for accommodation.

9. The artificial lens according to claim 1, further characterized in that it has a defined, pre-adjusted refractive power.

10. The artificial lens according to claim 1, further characterized in that it has a defined dynamic range of refractive power, and that the dynamic range comprises at least 1.5 diopters.

11. The artificial lens according to claim 1, further characterized in that the at least two media that are flexible in shape are provided in an uptake container forming the lens body, and that the media are fixed in space in uptake container.

12. The artificial lens according to claim 11, further characterized in that one medium that is flexible in shape is displaced or can be displaced in the direction of another medium that is flexible in shape each time via the means for changing the interface(s) in such a way that the curvature of at least one interface between the two media that are flexible in shape is altered.

13. The artificial lens according to claim 11, further characterized in that the means for changing the interface(s) can be disposed annularly around a clear opening.

14. The artificial lens according to claim 13, further characterized in that the clear opening at least corresponds to the maximum pupil diameter of the eye for which the artificial lens is specified.

15. The artificial lens according to claim 11, further characterized in that the means for changing at least one of the size and the shape of the interface(s) between the media that are flexible in shape are formed on the basis of electrowetting.

16. The artificial lens according to claim 15, further characterized in that a first medium that is flexible in shape and a second medium that is flexible in shape have a different electrical conductivity, that the medium that is flexible in shape and has the smaller electrical conductivity is disposed between the medium that is flexible in shape and has the greater electrical conductivity and at least one electrode, and that by applying an electrical field between the at least one electrode and the medium that is flexible in shape and has the greater electrical conductivity, the interface between the two media that are flexible in shape is changed or can be changed.

17. The artificial lens according to claim 11, further characterized in that the means for changing the interface(s) are designed so as to act on at least one of the media that are flexible in shape, the means for changing the interface(s) are designed so as to produce a pressure on at least one of the media that are flexible in shape, and that a medium that is flexible in shape is or can be displaced each time, and in particular, pressed, via this means, at least at an interface in at least one preferred direction, in the direction of another medium that is flexible in shape.

18. The artificial lens according to claim 17, further characterized in that the means for changing the interface(s) are formed as a mechanical means.

19. The artificial lens according to claim 18, further characterized in that the mechanical means are formed as a piston device, a stamping device or a cylinder device.

20. The artificial lens according to claim 17, further characterized in that the means for changing the interface(s) are designed in the form of at least one controllable membrane.

21. The artificial lens according to claim 11, further characterized in that at least one medium that is flexible in shape is surrounded on all sides by another medium that is flexible in shape, that the means for changing the interface(s) are designed so as to act on at least one of the media that are flexible in shape, and that the means for changing the interface(s) are designed for producing a pressure on at least one of the media that are flexible in shape.

22. The artificial lens according to claim 1, further characterized in that a control device is provided for controlling the artificial lens.

23. The artificial lens according to claim 1, further characterized in that the media that are flexible in shape cannot be mixed.

24. The artificial lens according to claim 1, further characterized in that at least one of the media that are flexible in shape is made transparent, at least in regions.

25. The artificial lens according to claim 1, further characterized in that the media that are flexible in shape have the same or approximately the same density.

26. The artificial lens according to claim 25, further characterized in that the media that are flexible in shape have the same or approximately the same density in a specific temperature range and that the temperature range may lie between 30° C. and 45° C.

27. The artificial lens according to claim 1, further characterized in that at least two of the media that are flexible in shape have different optical properties.

28. The artificial lens according to claim 1, further characterized in that means for stabilizing (stabilization means) the surface structure of at least one of the media that are flexible in shape are provided.

29. The artificial lens according to claim 28, further characterized in that the stabilization means are provided at least in the region of the interface(s) between two media that are flexible in shape.

30. An artificial lens for an eye, said artificial lens being a lens implant that is inserted into an eye in place of the natural lens of the eye, said artificial lens being characterized in that it has a lens comprising of two or more media that are flexible in shape that come into direct contact with one another, in that the at least two media that are flexible in shape are disposed in a lens body, in that the media that are flexible in shape contact on at least one interface and are disposed so that they can be displaced relative to one another, in that the media that are flexible in shape are each formed as a liquid or a type of gel, in that it has means for changing at least one of the size and shape of the at least one interface between the media, in that the media are applied to at least one bearing surface, at least in regions, said bearing surface being an intermediate layer inside said lens body, said intermediate layer having an opening which is made concentric around an optical axis of said artificial lens, said opening corresponding to the maximum pupil diameter of the eye for which the artificial lens is specified, and in that one of the media that are flexible in shape is made in the form of a drop, said medium being fixed in the region of said opening.

* * * * *